United States Patent [19]

Hach et al.

[11] 4,197,746
[45] Apr. 15, 1980

[54] SLURRY PIPET

[75] Inventors: Clifford C. Hach; Michael D. Buck, both of Loveland, Colo.

[73] Assignee: Hach Chemical Company, Loveland, Colo.

[21] Appl. No.: 960,752

[22] Filed: Nov. 15, 1978

[51] Int. Cl.² .............................................. G01N 1/12
[52] U.S. Cl. .............................................. 73/425.4 R
[58] Field of Search ............ 73/425.4 R, 425.6; 222/278, 288, 305

[56] References Cited

U.S. PATENT DOCUMENTS

| | | | |
|---|---|---|---|
| 1,603,712 | 10/1926 | Peck | 73/425.4 R |
| 1,887,859 | 11/1932 | Pearce | 73/425.4 R |
| 2,530,909 | 11/1950 | Riggs | 73/425.6 |
| 3,122,278 | 2/1964 | Crozier | 222/305 |
| 3,367,191 | 2/1968 | Richard | 73/425.6 |

Primary Examiner—S. Clement Swisher
Attorney, Agent, or Firm—Leydig, Voit, Osann, Mayer & Holt, Ltd.

[57] ABSTRACT

A pipet for slurry and the like comprising a body with an end chamber containing a slidable element which, between them, defines a predetermined volume. The element includes an end plate to close the chamber, and a biased plunger is mounted in the body for moving the element so as to open and close the chamber and thus trap the predetermined volume of material to be sampled. The element is replaceable with one of different size to vary the volume of sample. In one form, a cutting edge on the body and a cutting surface on the end plate cooperate to sever fibrous material only partly in the chamber.

2 Claims, 4 Drawing Figures

U.S. Patent  Apr. 15, 1980  4,197,746
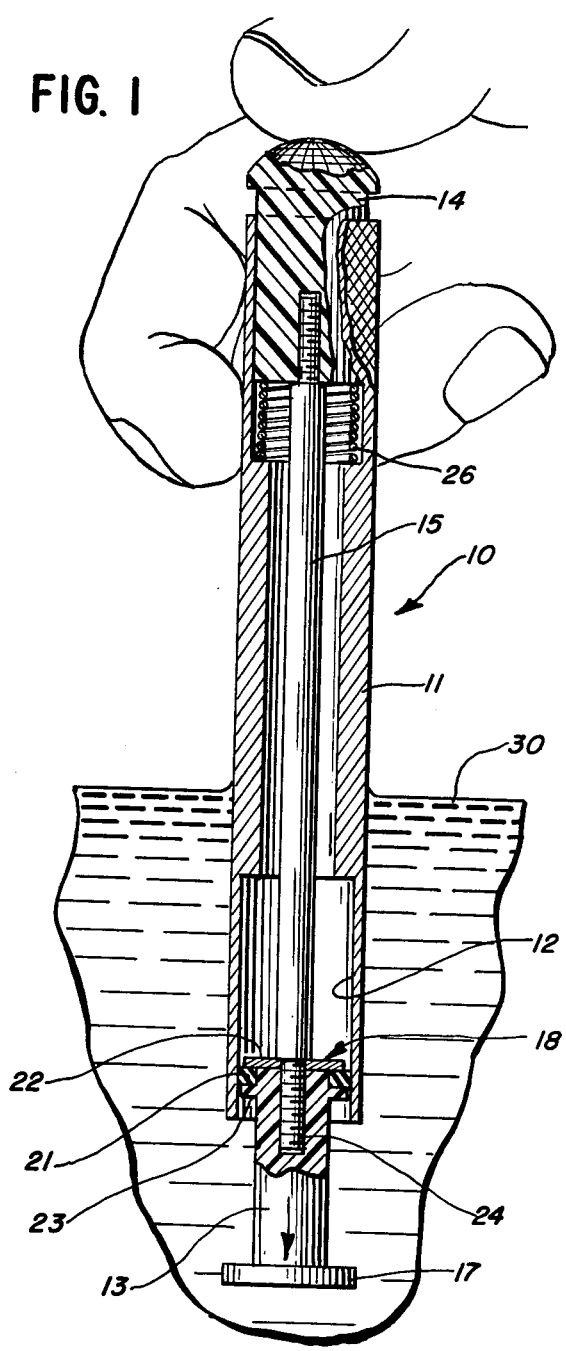
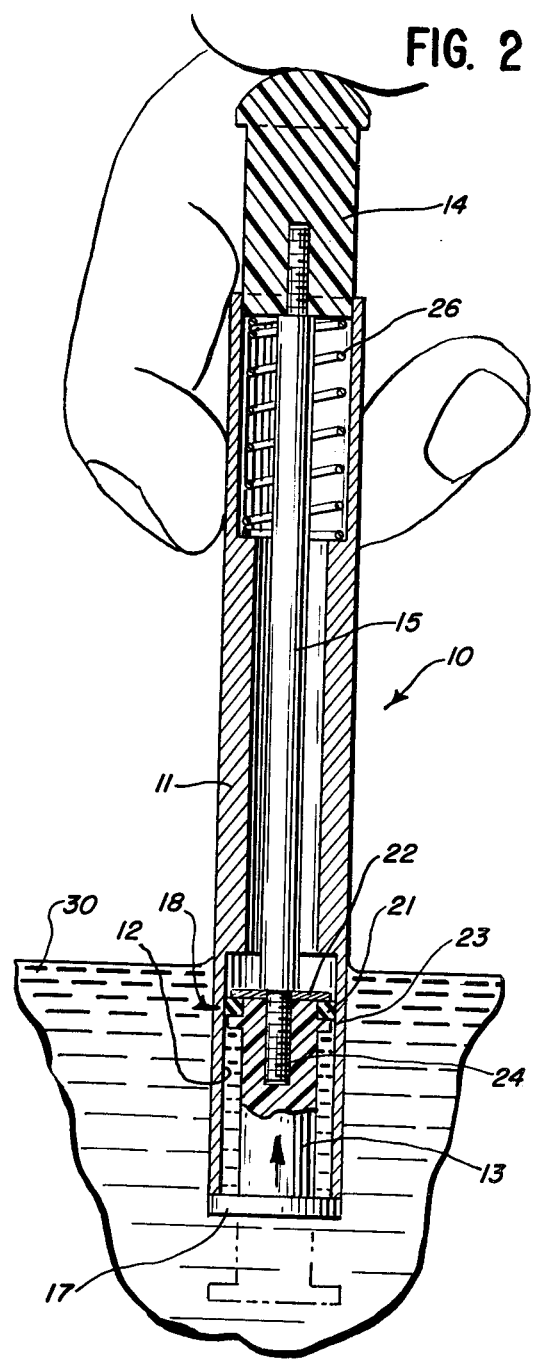
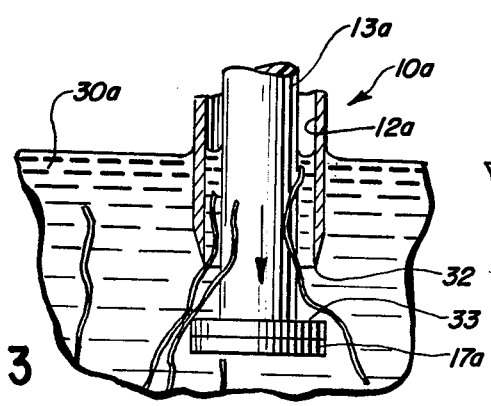
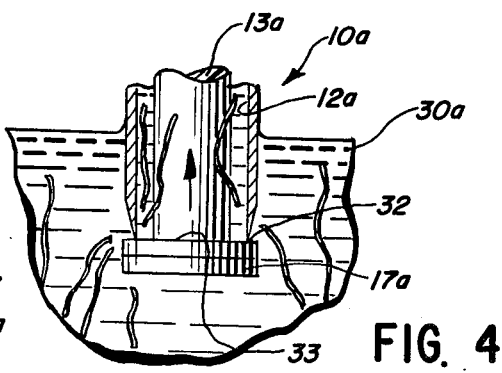

SLURRY PIPET

This invention relates generally to chemical test apparatus and more particularly concerns a pipet for obtaining accurately measured samples of materials that are virtually non-flowable.

To run chemical tests on materials existing in large volume, it is usually necessary to obtain an accurately measured sample of the material. For liquid materials, accurate sample volumes are conventionally obtained by using a pipet, but if the liquid is viscous or is a slurry or thick suspension, a conventional pipet will not drain. Nevertheless, there is a need for sampling for tests such diverse materials as catsup, well drilling mud, and liquid manure, which cannot be accurately measured in a conventional pipet.

Accordingly, it is the primary aim of the invention ot provide a pipet for highly viscous or slurry materials that accurately draws a sample of predetermined volume.

Another object of the invention is to provide a pipet of the above type which is easy to use, both with respect to taking a sample as well as cleaning the pipet for the next sample.

A further object is to provide a pipet as characterized above which can be quickly adjusted to draw samples of alternate predetermined volumes.

It is also an object to provide a pipet of the above kind that will clearly separate a representative sample containing long fibrous material by severing the fibers so that the sample is representative.

Other objects and advantages of the invention will become apparent upon reading the following detailed description and upon reference to the drawing, in which:

FIG. 1 is a longitudinal section of a pipet embodying the invention in its operated, sample obtaining configuration;

FIG. 2 is similar to FIG. 1 with the pipet in its sample containing configuration;

FIG. 3 is a fragmentary section similar to FIG. 1 showing an alternate form of the invention; and FIG. 4 is a fragmentary section similar to FIG. 2 showing the alternate embodiment appearing in FIG. 3.

While the invention will be described in connection with a preferred embodiment, it will be understood that we do not intend to limit the invention to that embodiment. On the contrary, we intend to cover all alternatives, modifications and equivalents as may be included within the spirit and scope of the invention as defined by the appended claims.

Turning to the drawing, there is shown in FIG. 1 a pipet 10 embodying the invention and including an elongated body 11 having a parallel wall, open-ended chamber 12 at one end, an element 13 slidably mounted in the chamber 12, and a plunger 14 in the body 11 coupled by a rod 15 to the element 13 for moving the element between limit positions, one shown in FIG. 2 and the other being approached in FIG. 1. The element 13 includes an end plate 17 that closes the end of the chamber 12 when the element 13 is in one limit position (FIG. 2). The element 13 also includes a piston portion 18 in sliding and sealing engagement with the wall of the chamber 12.

In the preferred embodiment, the body 11, chamber 12, element 13, end plate 17 and piston portion 18 are all cylindrical. The piston portion 18 is defined by an annular resilient washer 21 and a smaller rigid washer 22 sandwiched between a shoulder 23 on the element 13 and the end of a threaded, necked-down portion 24 of the rod 15. Preferably, the plunger 14 is connected by threads to the other end of the rod 15, and a helical spring 26 in the body 11 biases the plunger 14 outwardly and thus the element 13 to its FIG. 2 limit position.

In carrying out the invention, the element 13 and the chamber 12 are proportioned so as to define a predetermined volume between them when the end plate 17 closes the chamber. A practical such volume is 5 ml. Preferably, the head of the plunger and the upper outer portion of the body 11 is knurled so as to facilitate manual handling.

To take a sample, the pipet 10 has its chamber end immersed in the material 30 to be sampled, the plunger 14 is depressed and the pipet agitated to be sure that no air bubbles are trapped in the open end of the chamber 12. The plunger 14 is then released and the material constituting the sample is drawn up between the element 13 and the chamber 12, in the predetermined volume. The end of the pipet 10 is then washed off so that only the contents of the chamber 12 are conveyed to the desired receptacle. The plunger is again depressed to expose and discharge the sample and, in a typical procedure, the sample contacting parts of the pipet 10 are washed in a known quantity of demineralized water, such as 45 ml. of water for a 5 ml. sample, to produce a diluted sample of 50 ml. containing 10% of the material to be tested.

As a feature of the invention, the element 13 can be easily unthreaded from the rod 15 and replaced with an element of different proportions so as to selectively effect a change in the predetermined volume to be sampled.

As a modification, a pipet 10A, in which parts corresponding to those already described are given the same reference number with the distinguishing suffix A added, has its open chamber 12A formed with an end shaped to a cutting edge 32, and the end plate 17A on the element 13A carries a cutting surface 33 such as one side of a hard resilient washer. When the end plate 17A closes the chamber 12A, long fibrous materials interposed between the cutting edge 32 and the surface 33 are severed, thus keeping the measured volume of sample constant and representative of the mass of material 30A. The cutting action is facilitated by rotating the plunger, not shown, of the pipet 10A so as to slice through whatever fibers might be interposed between the cutting edge and the cutting surface.

It can now be seen that the pipets 10 and 10A are effective for providing accurately measured samples of highly viscous or slurry materials, and indeed, prototypes of such devices have been found to be accurate within 1%. It will be apparent that the structures are easy to use both with respect to taking a sample and with respect to delivering that sample or otherwise cleaning the pipet for its next use. The structures are simple and straightforward and thus are economical to manufacture and maintain.

We claim as our invention;

1. A pipet for slurry-like material comprising, in combination, a body having a parallel wall, open-ended chamber at one end, an element disposed in said chamber for sliding movement between two limit positions, said element having an end plate which closes the open end of said chamber when the element is in one limit position, said element also having a piston portion in sliding and sealing engagement with the chamber wall, said chamber and said element being proportioned so as to define a predetermined volume between them when the element is in said one limit position, a biased plunger mounted in said body and coupled to said element for manual movement of the element from said one limit position to open said chamber and back to said one limit position to enclose said predetermined volume of material between the element and the chamber, said open end of said chamber being shaped to a cutting edge, and said end plate including a cutting surface cooperating with said cutting edge to sever interposed material when the element is in said one limit position.

2. The combination of claim 1 in which said cutting edge and said cutting surface are circular, and said plunger allows said element to be manually rotated to facilitate said cutting action.

* * * * *